United States Patent [19]

Hazan et al.

[11] 4,406,028
[45] Sep. 27, 1983

[54] METHOD OF DETECTING THE RELEASE OF DYE FROM LAUNDRY DURING A WASHING OPERATION IN A WASHING MACHINE AND IMPLEMENTATION OF SAID METHOD

[75] Inventors: Jean-Pierre Hazan, Sucy-en-Brie; Michel Steers, Chennevieres-sur-Marne; Jean Caron, Evreux, all of France

[73] Assignee: U.S. Philips Corporation, New York, N.Y.

[21] Appl. No.: 274,935

[22] Filed: Jun. 18, 1981

[30] Foreign Application Priority Data

Jun. 18, 1980 [FR] France ................... 80 13536

[51] Int. Cl.³ .............................................. D06F 35/00
[52] U.S. Cl. ....................................... 8/158; 68/12 R; 356/72
[58] Field of Search ............ 8/158; 68/12 R; 356/72, 356/73

[56] References Cited

U.S. PATENT DOCUMENTS 3,114,253 12/1963 Morey et al. ................... 68/12 R
3,613,405 10/1971 Shimokusu et al. ............. 68/12 R
4,237,565 12/1980 Torita et al. ....................... 8/158

FOREIGN PATENT DOCUMENTS 1032498 6/1966 United Kingdom.

Primary Examiner—Philip R. Coe
Attorney, Agent, or Firm—Robert T. Mayer; Bernard Franzblau

[57] ABSTRACT

A method of detecting the release of dye from laundry in a washing machine despite the presence of dirt in the washing water. During a washing operation, a radiation flux including an infrared flux part ($\phi_I$) and a visible flux part ($\phi_V$) is passed through the wash water in which it is subject to absorption and diffusion. The flux parts $\phi_I$ and $\phi_V$ are compared during the entire washing program and the ratio of $\phi_V$ and $\phi_I$ is determined. The release of dye is signalled by a substantial variation of said ratio. The signal may be used for actuating an alarm device and/or controlling the washing program.

17 Claims, 9 Drawing Figures

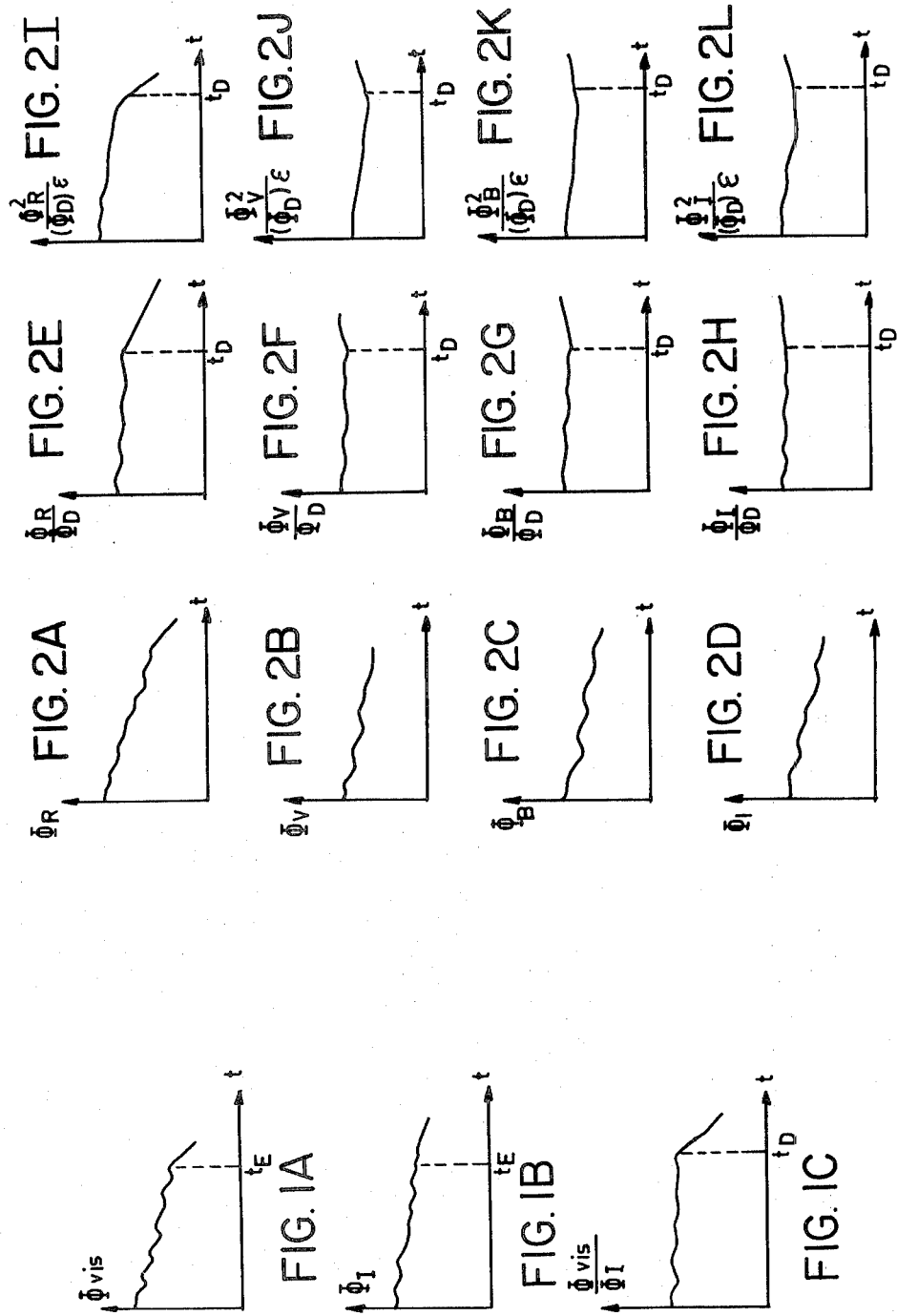

METHOD OF DETECTING THE RELEASE OF DYE FROM LAUNDRY DURING A WASHING OPERATION IN A WASHING MACHINE AND IMPLEMENTATION OF SAID METHOD

The present invention relates to a method of detecting the release of dye from laundry during a washing operation in a washing machine and the implementation of said method in order to prevent or stop said release of dye.

Release of dye from laundry is the process during which the dye in a piece of laundry of a certain colour (non-whites) is released into the detergent solution, via which solution said dye is transferred to other pieces of laundry which previously had a different colour, especially a white colour. A serious consequence of this process may be that certain pieces of laundry are rendered unsuitable for use so that it is necessary to prevent this effect and, once it occurs, to stop it before great damage is done.

In most cases dye release during the washing operation takes place when the water has reached a high temperature, which means that said washing operation is already in an advanced state. It follows that the washing water may already be soiled severely when dye release is likely to occur, or that the water is being soiled and contaminated with the dye at the same time.

One possible method of detecting said dye release is to measure the optical absorption of diffusion properties of the water contained in the machine during the entire washing process, from its beginning, specifically in those ranges of the light spectrum which correspond to the colours of the dyes contained in the laundry being washed. A release of one of said dyes, which presents the risk of staining, would result in an increased absorption or a change in the diffusion of light corresponding to the wavelengths of the colour of the dye being released. The result of such a method may be invalidated, especially when the water is soiled at the instant that the dye is released, so that it is no longer possible to make a clear distinction between the influence of soiling and the release of dye on the absorption or diffusion curves because the soiled water has a rather high opacity. Therefore, in the case of the simultaneous occurrence of soiling and the release of dye, an absolute spectral measurement of the absorption or diffusion no longer constitutes a criterion for the occurrence of dye release.

The method in accordance with the invention, however, is based on measurements of a radiation flux which has been subject to absorption and diffusion in the water in the machine. The invention is based on the fact that, to a first-order approximation and for a wide opacity range, the flux values measured in different spectral bands are each quantitatively influenced by the opacity of the soiled water in substantially the same proportion regardless of the spectral band being considered, whereas only the flux values measured in the spectral absorption bands of the released dye are influenced by said dye. Therefore, in order to detect the release of dye, the invention proposes to compare, during washing, the flux values corresponding to the spectral bands of the colour of the dye to a flux value (or a combination of flux values) which are influenced to a comparatively small extent by the colour of said dye.

More specifically, in a first embodiment of the method in accordance with the invention, a radiation flux which has been subject to absorption and diffusion in the washing water is measured, quasi-simultaneously and separately during the washing operation, in spectral bands involved in the release of dye and in bands not (or to a small extent) involved in said release, in order to determine ratios between, for each ratio, a linear combination of flux values measured in the spectral regions of the dye and a further linear combination of measured flux values which are hardly affected by said dye and to detect said dye release through the occurrence of substantial variations of at least one of said ratios as a function of time. Taking into account what has been stated in the foregoing, each ratio is generally a slowly varying function of time if no dye is released, whereas at least one of said ratios will vary substantially when dye is released.

Thus, in accordance with a variant of said first embodiment, the invention utilizes the fact that a large number of constituent colorants of the laundry dye exhibit a substantial absorption in one or a plurality of spectral bands in the visible spectrum (wavelength between 4000 and 7500 Å) and a very low absorption in certain bands of the near infrared region (which spectral bands may be narrow and whose wavelengths are situated between 7500 and 9500 Å). In accordance with this variant the radiation flux, after absorption and diffusion in the washing water, is measured separately in the near infrared region and in the visible spectral-absorption bands of the constituent colorants of the laundry dyestuffs. Ratios are determined between, for each ratio, a linear combination of flux values measured in the visible spectrum and the flux measured in the infrared region. Specifically, said combination may be restricted to the flux measured in one of the spectral bands of the visible light, such as for example red, green and blue, three ratios being thus examined.

In order to increase the sensitivity to dyes, in accordance with a second embodiment of the method in accordance with the invention which is a more general form of the first one, a comparison is made between a combination, which may be non-linear, of flux values measured in the visible spectrum and a further non-linear combination of flux values measured in the infrared region, as well as in the visible region. For example, components of the flux are measured in an infra-red band and in bands of the visible spectrum situated in the red, green and blue regions, $\phi_I$, $\phi_R$, $\phi_V$, and $\phi_B$ respectively, and the following ratios are determined $$\phi_N/\phi_D$$

in which $$\phi_N = a_1 \phi_R^{\alpha_1} + b_1 \phi_V^{\beta_1} + c_1 \phi_B^{\gamma_1}$$

$$\phi_D = a_2 \phi_R^{\alpha_2} + b_2 \phi_V^{\beta_2} + c_2 \phi_B^{\gamma_2} + d \phi_I^{\delta}$$

$a_1$, $b_1$, $c_1$ and $a_2$, $b_2$, $c_2$, d being coefficients which may be zero, $\alpha_1$, $\beta_1$, $\gamma_1$, $\alpha_2$, $\beta_2$, $\gamma_2$ and $\delta$ being positive exponents, and the coefficients $a_1$, $b_1$, $c_1$ and the exponents $\alpha_1$, $\beta_1$, $\gamma_1$ on the one hand and the coefficients $a_2$, $b_2$, $c_2$ and the exponents $\alpha_2$, $\beta_2$, $\gamma_2$ and $\delta$ on the other hand being selected in such a way that $\phi_N$ and $\phi_D$ respectively correspond to a high and low sensitivity to dyestuffs that are released.

Thus, in order to increase the sensitivity of the method for the detection of dye of a typical, particularly dangerous current colour, in accordance with a variant of said second embodiment, the contribution to the combination $\phi_N$ of the flux values measured in the spectral band relating to said dye is increased by raising the coefficients and/or the exponents relating to said flux values in said combination.

The method in accordance with the invention is implemented in laundry washing machines by equipping said machines with suitable detectors which each, in a spectral band of the visible or infrared range, measure the radiation flux which issues from a source and has been subject to absorption and diffusion in the laundry washing water inside a receptacle having transparent walls and being in communication with the washing tub of the machine. Measuring means are provided which process the signals supplied by the detectors and which combine the signals which are or which are not influenced by the released dye and which determine the ratios between said combinations, and means, comprising a memory element, for detecting sudden variations of said ratios when dye is released. The means for computing and detecting said sudden variations, for example, may employ microprocessors.

The invention proposes different arrangements for the radiation sources and detectors in the machine and in particular an arrangement of the sources and detectors around a transparent vessel. This vessel communicates with the tub and can be filled with washing water. In the case of a machine having a front door, the vessel may be integrated in the door and the sources and detectors may be arranged on the door, means being provided which prevent the detectors from being influenced by light from outside the machine.

Embodiments of the invention will now be described in more detail with reference to the accompanying drawings, in which:

FIG. 1 represents a series of graphs which illustrate a first variant of a first embodiment of the method in accordance with the invention;

FIG. 2 represents a series of graphs which illustrate a second variant of a first embodiment and a variant of a second embodiment of the method in accordance with the invention, FIG. 3 schematically represents a device for carrying out the method in accordance with the invention in accordance with a first variant;

Figure 3:
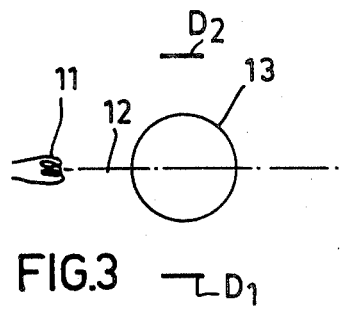
Figure 4:
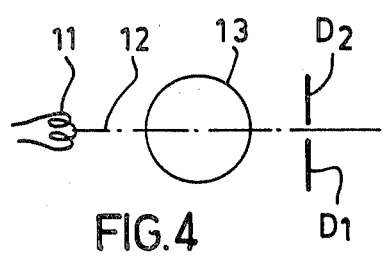
Figure 5:
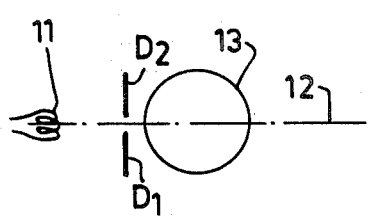
Figure 6:
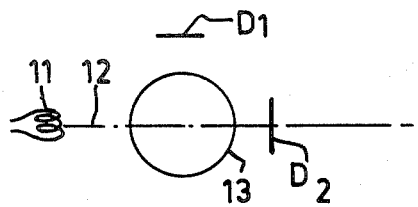
Figure 7:
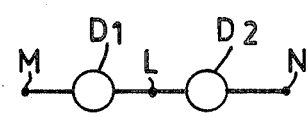
Figure 8:
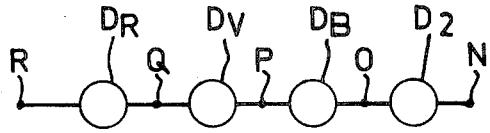

FIG. 4 schematically represents a second variant of the device for carrying out the method in accordance with the invention;

FIG. 5 schematically represents a third variant of a device for carrying out the method in accordance with the invention;

FIG. 6 schematically represents a fourth variant of the device for carrying out the method in accordance with the invention;

FIG. 7 is a diagram showing the electrical connections of the photoelectric detector used in the case of two detectors;

FIG. 8 shows a diagram indicating the electrical connections of the photoelectric detectors employed in the case of n detectors, when n=4.

Figure 9:
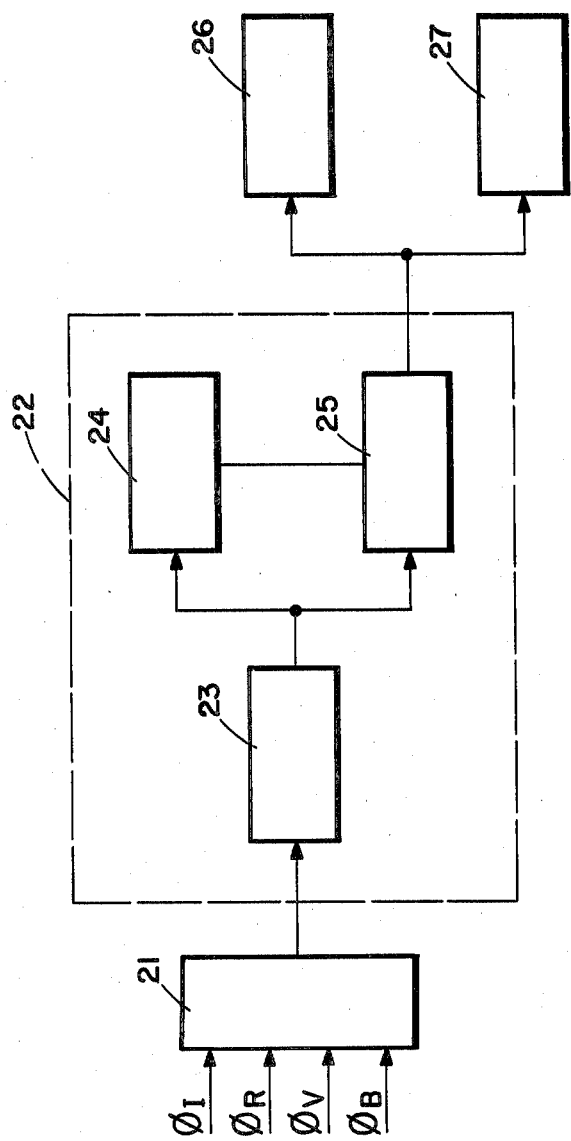

FIG. 9 is a block diagram of an apparatus for carrying out the method in accordance with the invention.

FIG. 1 relates to a variant of the first embodiment of the method in accordance with the invention. In this embodiment it is assumed that dye is released while the washing water is highly soiled and the constituent colorants of the dye of the laundry being washed exhibit a high absorption in the visible region (wavelength from 4000 to 7,500 Å) but a low absorption in the infrared region (spectral band of wavelengths between 7,500 and 9000 Å, which band may be very narrow). Said Figure shows three graphs, A, B and C with rectangular coordinate axes. The horizontal axis represents the time t which has elapsed since the beginning of the washing operation. The ordinates of A and B respectively indicate the visible portion $\phi_{vis}$ and the infrared portion $\phi_I$ of a radiation flux (broad system) after absorption and diffusion in a certain volume of washing water. $\phi_{vis}$ and $\phi_I$ are both decreasing functions of time. If for a value $t_E$ of t the decrease of $\phi_I$ or of $\phi_{vis}$ becomes very large, this corresponds without any doubt to a substantial soiling of the water for $\phi_I$, but for $\phi_{vis}$ this may either be the result of a substantial soiling of the water or the release of dye with a high absorption of visible light of the same colour as the dye, or both effects at the same time. In order to ascertain this, the ratio $\phi_{vis}/\phi_I$ is formed, which is represented as a function of time in the graph C of FIG. 1. Said ratio varies only slightly before $t_E$. If it decreases substantially at an instant $t_D$ near $t_E$, this indicates a sudden variation of the absorption in the visible spectrum caused by a release of dye into the washing water. The fact that the water becomes opaque manifests itself in a similar way for the visible portion $\phi_{vis}$ and the infrared portion $\phi_I$ of the flux, which becomes apparent as the virtual constancy of the ratio $\phi_{vis}/\phi_I$ near the instant $t_E$ and before $t_D$. However, the constituent colorants of the dye exhibit hardly any absorption band in the infrared region but only in the visible region which, in the case of dye release explains the fact that $\phi_{vis}$ decreases more strongly than $\phi_I$, which manifests itself as a substantial decrease of $\phi_{vis}/\phi_I$.

Further variants are possible to this first embodiment. For example, in order to increase the detection sensitivity, the measurements of the flux in the visible region may be effected in limited spectral bands in which the constituent colorants of the dye are absorbed. Thus, the measurement may for example be carried out in three spectral bands, such as the bands situated in the red, green and blue regions of the visible spectrum, the corresponding flux values measured being $\phi_R$, $\phi_V$ and $\phi_B$ respectively. The method is explained with reference to FIG. 2, which slows the series of graphs ABCD, EFGH and IJKL respectively with rectangular coordinate axes, the horizontal axis denoting the time t which has elapsed since the beginning of the washing operation. In A, B, C, D the ordinates indicate the red, green, blue and infrared components, $\phi_R$, $\phi_V$, $\phi_B$ and $\phi_I$ respectively, as a function of time of a radiation flux with a broad spectrum (white light) after absorption and diffusion in a certain volume of washing water. Since the concentration of soil particles in the water increases with time, the opacity of the water increases as a function thereof. If allowance is made for a said opacity only, the component $\phi_R$, $\phi_V$, $\phi_B$ and $\phi_I$ and decreasing functions of time, as is shown in A, B, C, D. Each of said flux values is compared with the linear combination:

$$\phi_D = a\phi_R + b\phi_V + c\phi_B + d\phi_I$$

of said different flux values, abcd being coefficients, some of which may be zero and which are adjusted in such a way that $\phi_D$ remains substantially independent of a release of dye in one of the colours, for example red. The graphs EFGH of FIG. 2 represent the variations of said ratios. The release of dye in the red region manifests itself in the graph E as a substantial decrease of the ratio $\phi_R/\phi_D$ at the instant $t_D$ at which dye in the red region is released and in the graphs, F, G, H as a slight variation of the other ratios. In FIG. 2 the combination $\phi_D$ in the denominator is the same for all the graphs when a dye release in the red region is to be detected. For the detection of a release of dye in the green or the blue region said linear combination $\phi_D$ should be modified so that it becomes insensitive to green and to blue.

In accordance with further variants of said first embodiment a comparison is made between a linear combination $\phi_N$ of flux values measured in certain dye-release bands, for example $\phi_B$ and $\phi_R$, and another combination $\phi_D$ of measured flux values which are influenced to a very small extent by the release of dye because in said other combination the coefficients of the combination have been chosen so that a great weight is attributed to a flux value which is not affected by dye release. The ratio of the combinations which are compared may for example be:

$$\frac{\phi_N}{\phi_D} = \frac{a\phi_B + b\phi_R}{c\phi_B + d\phi_R + e\phi_I}$$

where c, d and e are such that $c\phi_B+d\phi_R$ remains small relative to $e\phi_I$. As a result variations of said ratio are very sensitive to a substantial variation of $\phi_B$ or $\phi_R$ caused by a release of dye in one of the colours blue or red. In a second embodiment of the invention, in order to increase the sensitivity to the release of dye, $\phi_N$ and $\phi_D$ need no longer be only linear combinations of the flux values measured in the various spectral bands, but may also be positive powers of said flux values. The graphs I, J, K, L of FIG. 2 illustrate a variant of said second embodiment. In order to increase the sensitivity, the respective ratios of $\phi_R^2$, $\phi_V^2$ to $(\phi_D)^\epsilon$ have been considered, $\phi_D$ being the same combination as in the graphs E, F, G, H which relate to a variant of the first embodiment of the method, and $\epsilon$ being a positive exponent, for example equal to 2.

Before dye is released, for example in the red region, all these ratios are substantially constant or decrease slightly as a function of time with a greater slope than on the graphs E, F, G, H. At the instant $t_D$ at which dye is released, the ratio $\phi_R^2/(\phi_D)^\epsilon$ exhibits a stronger decrease on the graph I than the ratio $\phi_R/\phi_D$ on the graph E, so that the detection sensitivity to said dye release is improved.

FIGS. 3 to 8 show how the method in accordance with the invention is carried out. In these Figures the reference 11 designates a radiation source in the form of, for example, an incandescent lamp which emits radiation in the visible and infrared regions. The axix of the radiation diagram, which is situated in the plane of the drawing, is referenced 12. The reference 13 denotes the, for example circular, section through the plane of the drawing of a receptacle which is transparent to the radiation emitted by the lamp and which communicates with the tub of the washing machine. The flux values mentioned in the foregoing and represented in FIGS. 1 and 2 are each measured with the aid of a detector which may be provided with a spectral filter, in such a way that the combination of the detector and filter is sensitive to the wavelengths of the radiation constituting said flux values, which flux values are each converted into an electric signal. The detectors, of which there are at least two, may be arranged differently relative to the receptacle. Said detectors $D_1$ and $D_2$, in accordance with the variant of FIG. 3, may both receive the light which has been diffused by the water. They are disposed outside the direct beam emitted by 11, for example one on each side of the axis 12 on a diameter of 13. In that case the flux values measured contain a substantial portion of diffused radiation which has also been subject to absorption in the water in proportion to the thickness of the volume of water through which it has passed. The detector $D_1$ is for example intended for a visible part of the spectrum, whereas the detector $D_2$ serves for the infrared part.

In the variant of FIG. 4 the detectors $D_1$ and $D_2$ both receive a part of the direct flux (not diffused) emitted by radiation source 11. They are for example situated one on each side of the axis 12, but practically opposite to 11. In order to facilitate mounting, the direct beam may be directed at the detectors $D_1$ and $D_2$, which are arranged at readily accessible locations, by means of mirrors. In the case of such an arrangement it is the absorption which especially contributes to the flux measurement.

In the variant of FIG. 5 the detectors $D_1$ and $D_2$ are disposed one on each side of the axis 12, but on the same side as the source 11 relative to the section 13. Such an arrangement ensures that both the diffusion and absorption contribute to the flux measurement. In the case of a washing machine with a transparent front door, said arrangement has the advantage that it can easily be arranged at the front of the machine. In the variant of Figure 6 the detector $D_2$ receives the direct flux and detector $D_1$ the diffused flux. It is evident that for the detection of the visible light in various separate bands of the spectrum the number of detectors should correspond to the number of bands. Moreover, it is obvious that for carrying out the method, instead of a source with a broad-band spectrum which is optically filtered upon detection, use may be made of a plurality of narrow-band sources which emit radiation in the infrared region and in absorption bands of the dyes in the visible region.

FIG. 7 shows an electric circuit arrangement which may be used for the detectors. The detectors $D_1$ and $D_2$, which are suitably energized, are connected in series and a signal proportional to the flux $\phi_{vis}$ is available across the terminals M and L, while signals proportional to a linear combination $a\phi_{vis}+b\phi_I$ or to $\phi_I$ are available across the respective terminals M and N or N and L. The gain factors of the detectors and the filter have been selected in such a way that $b\phi_I$ preponderates over $\phi_{vis}$, said signals being subsequently processed by means such as an operational amplifier and a memory element or rather a microprocessor which forms the ratio of said signals and which supplies a signal which is proportional to $\phi_{vis}/\phi_I$ or $\phi_{vis}/(a\phi_{vis}+b\phi_I)$, whose sudden variation indicates the release of dyestuff.

FIG. 8 shows an electric circuit arrangement which may be used if the visible radiation after absorption and diffusion is measured both in the red, green and blue regions. Said detector $D_1$ is divided into three detectors $D_R$, $D_V$ and $D_B$ which are only sensitive to red, green and blue respectively. Said detectors are arranged in series with the detector $D_2$, the respective terminals being N, O, P, Q, R. The detectors $D_2$, $D_R$, $D_V$, $D_B$ produce a signal at their terminals which is proportional to $\phi_I$, $\phi_R$, $\phi_V$ and $\phi_B$ respectively. As in the foregoing, the various signals available at the relevant terminals are processed by processing means such as, for example, microprocessors, which serve to provide a combination of signals proportional to a linear combination of the form:

$\phi = a\phi_I + b\phi_R + c\phi_V + d\phi_B$ as defined in the foregoing, and to form the ratios between the signal corresponding to one of the red, green, blue or infrared components and the combination signal. A release of dye in one of said colours is then signalled by a sudden variation as a function of time of the ratio thus calculated and corresponding to said colour, the relative variation of the ratio relating to the colour of the dye that is released being substantially greater than those of the other ratios.

FIG. 9 describes in block diagram form an example of the implementation of signal and data processing incorporating a microprocessor. The signals from detectors $D_2$, $D_R$, $D_V$, $D_B$ (FIG. 8) and corresponding to the light flux $\phi_I$, $\phi_R$, $\phi_V$, $\phi_B$ are first measured and converted in a signal processing and analog to digital converter unit 21 and are then introduced into a microprocessor 22. The latter includes three functional elements: a computation unit 23 which receives the signals supplied from unit 21, and in which is derived the ratio of the combination of signals described previously. A memory unit 24 in which the ratios coming from computation unit 23 are periodically stored and a comparator 25 which compares the ratio signals from unit 23 with the ratios stored in memory unit 24 and corresponding to a previous measurement. If the two values introduced into the comparator are appreciably different, the comparator delivers a signals to an alarm 26 and/or to a program control unit 27 which will perform a suitable programmed action.

The device for carrying out the method in accordance with the invention may be used for actuating an alarm and/or changing the washing program. The signal which indicates the release of dye serves to control the actuation of an alarm and/or to control the devices controlling the washing program in order to change said program, for example, by switching off the heating and admitting cold water.

What is claimed is:

1. A method of detecting the release of one or more dyes from laundry in an automatic washing machine during a washing operation which comprises, during said washing operation, passing a luminous flux comprising light in the visible and the infrared part of the spectrum through a certain volume of the washing water where said luminous flux is subject to absorption and diffusion, simultaneously and separately measuring the luminous flux in the visible region and in the infrared region after absorption and diffusion thereof, the visible region including one or a plurality of absorption bands for said dyes, subsequently determining the ratios between the measurement results obtained in the visible region and a combination of measurement results obtained in both the visible and the infrared region, the last-mentioned combination being only affected to a small extent by the release of dye, and detecting the release of dye by the detection of variations of at least one of said ratios as a function of time.

2. A method as claimed in claim 1, characterized in that the said combination is a linear combination of luminous flux values measured in a plurality of spectral bands of visible and infrared light.

3. A method as claimed in claim 1, characterized in that the combination is a combination of flux values measured in each of the spectral bands in the visible and the infrared region raised to powers with a positive exponent.

4. A method as claimed in any one of the claims 1 to 3, characterized in that the absorption bands of the colorants in the visible part of the spectrum are measured in the red, green and blue spectral bands.

5. A device for detecting the release of dye from laundry in an automatic washing machine comprising, a source of light which emits light in the visible and infrared region of the spectrum, a light transparent receptacle which communicates with the washing tub and is exposed to said light, first and second detectors, one of which is sensitive to infrared and the other to the visible part of the spectrum, said detectors being arranged near said receptacle opposite one wall thereof, means for measuring the signals supplied by the detectors and for calculating at least one ratio of measurement results obtained in the visible part of the spectrum over a combination of measurement results obtained in the visible and the infrared part of the spectrum, and means for detecting variations of said ratios as a function of time.

6. A device as claimed in claim 5, characterized in that the detector which is sensitive to the visible part of the spectrum comprises a plurality of detectors which are sensitive to different spectral bands.

7. A device as claimed in claim 5 or 6, characterized in that the light source is divided into a plurality of different light sources with narrow spectral bands.

8. A method of detecting the release of one or more dyes from laundry in a washing machine during a washing operation which comprises, passing a radiation flux comprising light in the visible and the infrared parts of the spectrum through a given volume of the wash water in which said radiation flux is subject to absorption and diffusion, detecting the radiation flux in the visible region of the spectrum after absorption and diffusion thereof by the wash water, the visible region including on or more absorption bands for the dyes, detecting the radiation flux in the infrared region of the spectrum after absorption and diffusion thereof by the wash water, the release of dye having a relatively small effect on the radiation flux detected in the infrared region, and forming ratios between the radiation flux detected in the visible region and the combined radiation flux detected in both the visible and infrared regions, the release of dye being signalled by a variation of at least one of said ratios as a function of time.

9. A method as claimed in claim 8 wherein the ratio formed is the ratio of the radiation flux detected in the visible region of the spectrum to the radiation flux detected in the infrared region.

10. A method as claimed in claim 8 wherein the ratio $\phi_N/\phi_D$ is formed, where $\phi_N = a_1\phi_R{}^{\alpha_1} + b_1\phi_V{}^{\beta_1} + c_1\phi_B{}^{\gamma_1}$; $\phi_D = a_2\phi_R{}^{\alpha_2} + b_2\phi_V{}^{\beta_2} + c_2\phi_B{}^{\gamma_2} + d\phi_I{}^{\delta}$; where $a_1$, $b_1$, $c_1$, and $a_2$, $b_2$, $c_2$, $d$ are coefficients one or more of which may be zero and $\alpha_1$, $\beta_1$, $\gamma_1$ and $\alpha_2$, $\beta_2$, $\gamma_2$ and $\delta$ are positive exponents, and wherein the values of said coefficients and exponents can be chosen to increase the detection sensitivity to one or more particular colors of dye in the visible spectrum.

11. A method as claimed in claim 8 wherein one or more of the ratios $\phi_R/\phi_D$, $\phi_V/\phi_D$ and $\phi_B/\phi_D$ are formed, where $\phi_R$, $\phi_V$ and $\phi_B$ are the radiation fluxes detected in the red, green and blue regions of the visible spectrum, respectively, and $\phi_D = a\phi_R + b\phi_V + c\phi_B + d\phi_I$, where a, b, c and d are coefficients one or more of which can be zero and $\phi_I$ is the radiation flux detected in the infrared region of the spectrum.

12. A method as claimed in claim 8 wherein one or more of the ratios $\phi_R^2/(\phi_D)^\epsilon$, $\phi_V^2/(\phi_D)^\epsilon$, and $\phi_B^2/(\phi_D)^\epsilon$ are formed, where $\phi_R$, $\phi_V$, $\phi_B$ and $\phi_D$ are defined in claim 11 and $\epsilon$ is a positive exponent.

13. An apparatus for detecting the release of dye from laundry in a washing machine comprising, a source of radiation flux which emits in the visible and infrared region of the spectrum and is positioned so that wash water for the machine is subject to said radiation flux, at least first and second radiation detectors one of which is sensitive to radiation flux in the visible part of the spectrum and the other one being sensitive to radiation flux in the infrared region of the spectrum, said detectors being located to detect the radiation flux from the radiation source after it has been subject to absorption and diffusion by said wash water and to produce a first signal determined by the radiation flux in the visible part of the spectrum and a second signal determined at least in part by the radiation flux in the infrared region of the spectrum so that a ratio of said first and second signals can be determined and the release of dye indicated by a characteristic variation of said ratio as a function of time.

14. An apparatus as claimed in claim 13 further comprising means for combining said first and second signals to form a ratio of $\phi_{vis}/(a\phi_{vis}+b\phi_I)$ where $\phi_{vis}$ and $\phi_I$ are signals determined by the detected flux in the visible and infrared regions of the spectrum and a and b are coefficients.

15. Apparatus as claimed in claim 13 wherein said first detector is sensitive only to the red region of the spectrum and the second detector is sensitive only to the infrared region of the spectrum, said apparatus further comprising third and fourth radiation detectors sensitive only to the green and blue regions of the spectrum, respectively, and located to detect the radiation flux from the radiation source after absorption and diffusion thereof by the wash water and to derive third and fourth signals determined by green and blue components of dye in the wash water, and means for combining the signals from said detectors to form one or more of the following ratios: $\phi_R/\phi_{comb}$, $\phi_V/\phi_{comb}$ and $\phi_B/\phi_{comb}$, where $\phi_R$, $\phi_V$ and $\phi_B$ are the first, third and fourth signals corresponding to the colors red, green and blue, and $\phi_{comb}$ is a signal defined by: $\phi_{comb}=a\phi_I+b\phi_R+c\phi_V+d\phi_B$, where $\phi_I$ is the second signal corresponding to the infrared region of the spectrum and a, b, c and d are coefficients.

16. Apparatus as claimed in claim 15 wherein said combining means includes circuit means for connecting said first, second, third and fourth detectors in series circuit and providing intermediate terminals for tapping off said first, third and fourth signals and end terminals for supplying said combination signal $\phi_{comb}$.

17. An apparatus as claimed in claim 14 wherein said visible part of the spectrum encompasses the wavelengths between 4000 and 7500 Å and said infrared region includes the wavelengths between 7500 and 9500 Å.

* * * * *

UNITED STATES PATENT AND TRADEMARK OFFICE
CERTIFICATE OF CORRECTION

PATENT NO. : 4,406,028
DATED : September 27, 1983
INVENTOR(S) : JEAN-PIERRE HAZAN ET AL It is certified that error appears in the above-identified patent and that said Letters Patent is hereby corrected as shown below:

Claim 15, line 17, please change the formula from "= a $\phi_I$ + b $\phi_R$ + c $O_V$ + d $\phi_B$" to -- a $\phi_I$ + b $\phi_R$ + c $\phi_V$ + d $\phi_B$ --

Signed and Sealed this

Ninth Day of October 1984

[SEAL]

*Attest:*

*Attesting Officer*

GERALD J. MOSSINGHOFF

*Commissioner of Patents and Trademarks*